United States Patent
Decottignies et al.

(10) Patent No.: US 9,156,040 B2
(45) Date of Patent: Oct. 13, 2015

(54) FLUID PRODUCT DISPENSING HEAD

(75) Inventors: Laurent Decottignies, Cergy (FR);
Ludovic Goudigan, Epinay (FR)

(73) Assignee: APTAR FRANCE SAS, Le Neubourg (FR)

( * ) Notice: Subject to any disclaimer, the term of this patent is extended or adjusted under 35 U.S.C. 154(b) by 25 days.

(21) Appl. No.: 13/816,821

(22) PCT Filed: Aug. 23, 2011

(86) PCT No.: PCT/FR2011/051947
§ 371 (c)(1),
(2), (4) Date: Apr. 4, 2013

(87) PCT Pub. No.: WO2012/025691
PCT Pub. Date: Mar. 1, 2012

(65) Prior Publication Data
US 2013/0181014 A1 Jul. 18, 2013

(30) Foreign Application Priority Data
Aug. 26, 2010 (FR) ...................................... 10 56794

(51) Int. Cl.
*G01F 11/00* (2006.01)
*G01F 11/10* (2006.01)
(Continued)

(52) U.S. Cl.
CPC . *B05B 1/22* (2013.01); *A45D 34/04* (2013.01); *A61M 35/003* (2013.01);
(Continued)

(58) Field of Classification Search
CPC ............................... B05B 11/0091; B05B 1/22
USPC ................ 222/321.1, 321.7, 321.9, 526–527, 222/321.8, 402.21–402.23, 321.3, 402.12, 222/402.13
See application file for complete search history.

(56) References Cited

U.S. PATENT DOCUMENTS

2007/0017938 A1* 1/2007 Thompson et al. ........... 222/527
2007/0075097 A1 4/2007 Behar et al.
(Continued)

FOREIGN PATENT DOCUMENTS

EP 1 842 799 A1 10/2007
FR 2 483 262 A1 12/1981
(Continued)

OTHER PUBLICATIONS

International Search Report of PCT/FR2011/051947, dated Nov. 3, 2011.

*Primary Examiner* — Paul R Durand
*Assistant Examiner* — Jeremy W Carroll
(74) *Attorney, Agent, or Firm* — Sughrue Mion, PLLC

(57) ABSTRACT

A fluid dispenser head for mounting on an axial actuator rod (31) of a dispenser member (3), the head comprising an inner core (1) and an outer casing (2), the core (1) forming a connection sleeve (11) of axis (X) for mounting on the axial actuator rod (31), the casing (2) forming a dispenser endpiece (23) that is elongate and that is offset relative to the axis (X), the dispenser head being characterized in that the core (1) forms a deformable cannula (14) that is connected to the connection sleeve (11) and that extends in the endpiece (23) of the casing (2), said cannula forming a first section (14a) that is substantially rectilinear and that extends transversely relative to the axis X, a second section (14b) that is bent, and a third section that is inserted into the dispenser endpiece (23), the cannula (14) initially being rectilinear over its entire length and then being deformed while it is being inserted into the endpiece (23).

14 Claims, 1 Drawing Sheet

(51) Int. Cl.
  *B05B 1/22* (2006.01)
  *A45D 34/04* (2006.01)
  *A61M 35/00* (2006.01)
  *B65D 83/20* (2006.01)
  *B05B 11/00* (2006.01)
  *B65D 83/30* (2006.01)
  *B65D 83/40* (2006.01)

(52) U.S. Cl.
  CPC ......... *B05B 11/0089* (2013.01); *B65D 83/205* (2013.01); *B65D 83/30* (2013.01); *A45D 2200/15* (2013.01); *B65D 83/40* (2013.01); *Y10T 29/49236* (2015.01)

(56) References Cited

U.S. PATENT DOCUMENTS

| | | | |
|---|---|---|---|
| 2008/0314934 A1* | 12/2008 | Decottignies et al. | 222/321.3 |
| 2009/0039114 A1* | 2/2009 | Yamamoto et al. | 222/402.14 |
| 2009/0050650 A1* | 2/2009 | Walters et al. | 222/153.11 |
| 2010/0170917 A1* | 7/2010 | Ki | 222/256 |
| 2012/0000930 A1* | 1/2012 | Barbieri | 222/1 |

FOREIGN PATENT DOCUMENTS

| | | |
|---|---|---|
| FR | 2 860 768 A1 | 4/2005 |
| FR | 2 884 157 A1 | 10/2006 |
| WO | 2009/025697 A1 | 2/2009 |

* cited by examiner

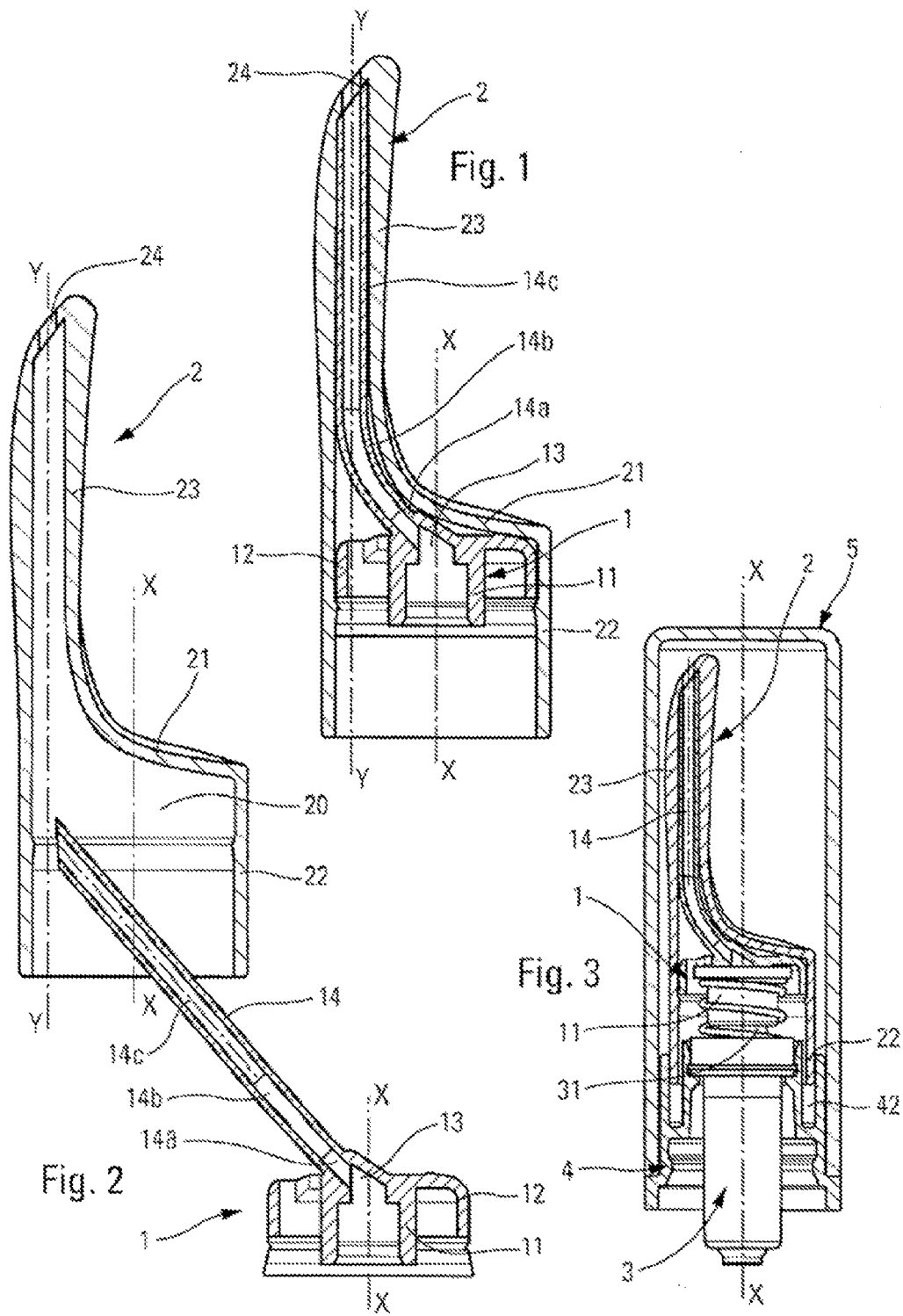

FLUID PRODUCT DISPENSING HEAD

CROSS REFERENCE TO RELATED APPLICATIONS

This is a National Stage of International Application No. PCT/FR2011/051947 filed Aug. 23, 2011, claiming priority based on French Patent Application No. 1056794 filed Aug. 26, 2010, the contents of all of which are incorporated herein by reference in their entirety.

FIELD OF INVENTION AND BACKGROUND

The present invention relates to a fluid dispenser head for mounting on an axial actuator rod of a dispenser member, such as a pump. The head comprises an inner core and an outer casing, the core forming a connection sleeve of axis X for mounting on the axial actuator rod, the casing forming a dispenser endpiece that is elongate and that is offset relative to the axis. Such a dispenser head is known in particular from document FR 2 860 768. The dispenser head finds an advantageous application in the field of cosmetics, but may also be used in the fields of pharmacy and perfumery. The present invention also relates to a method of manufacturing such a dispenser head.

In above-mentioned document FR 2 860 768, the core forms an axial spout that is inserted into the axial dispenser endpiece formed by the casing. The spout defines a groove that is open along its length and that is completed by the casing so as to form a feed channel connecting the connection sleeve of the core to the free end of the dispenser endpiece of the casing. The core is made out of a rigid plastics material, such that the spout is not deformable. In contrast, it is envisaged to form the outer casing with a plastics material that is relatively flexible so as to impart flexibility to the free end of the dispenser endpiece. With such a configuration, the core is inserted axially into the casing, the spout of the core already being in alignment with the dispenser endpiece of the casing. Neither the core nor the casing are subjected to significant deformation that would modify the general appearance of the dispenser head.

However, the dispenser head suffers a drawback that is associated with the formation of the feed channel connecting the sleeve to the free end of the dispenser endpiece. The disadvantage results from the feed channel being formed by assembling the core inside the casing, and as a result requires intimate sealing contact between the core and the casing, so as to isolate the feed channel completely without any risk of leakage. Theoretically, this seems possible, but in practice, it turns out that it is impossible to isolate the feed channel completely. Fluid leakage between the core and the casing has been found. The fluid that leaks deteriorates and then contaminates the fluid that is dispensed through the feed channel. Consequently, the configuration of the feed channel of the prior-art dispenser head does not guarantee complete preservation of the fluid that is dispensed. This is a major drawback, in particular with particularly delicate fluids.

In addition, the design of the dispenser head of document FR 2 860 768 requires using, for the casing, materials that are compatible with the fluid to be dispensed, given that the feed channel is formed both by the core and by the casing. This considerably reduces the choice of material used to make the casing, which material must also impart an attractive appearance, since it can be seen.

BRIEF SUMMARY OF CERTAIN OBJECTS AND ASPECTS OF INVENTION

An object of the invention is to remedy the above-mentioned drawbacks of the prior art by defining a novel design for a dispenser head of that type that eliminates any risk of fluid leakage at the feed channel connecting the dispenser sleeve to the dispenser orifice of the endpiece of the casing.

To do this, the present invention makes provision for the core to form a deformable feed cannula that is connected to the connection sleeve and that extends in the endpiece of the casing, the cannula initially being rectilinear over its entire length, and then being deformed while it is being inserted into the endpiece. The deformable cannula may be made integrally with the remainder of the core, or, in a variant, the deformable cannula may be fitted or over-molded onto the core. In contrast to the above-mentioned prior art, the cannula that connects the connection sleeve to the dispenser orifice is formed only by the core, and not by assembling together the core and the casing. Thus, the casing may be made out of any material, and even a material that is incompatible with the fluid to be dispensed. In addition, any risk of leakage along the cannula is thus eliminated. Furthermore, by making the cannula in rectilinear manner, it is possible to make the core by injection molding with mold elements that are relatively simple. The core is inserted into the casing in the same way as in the prior art, except for the cannula that is deformed during this operation.

In a practical embodiment, the cannula may present a wall thickness that is less than the wall thickness of the connection sleeve, so as to impart flexibility thereto. The cannula may even present various wall thicknesses along its length. By way of example, the bent second section may present a wall thickness that is less than the wall thickness of the other two sections that are not deformed. It is also possible to envisage making the cannula with a material that is more flexible than the remainder of the core.

In another aspect of the present invention, the cannula may extend over substantially the entire length of the endpiece. Thus, no fluid flows in contact with the dispenser endpiece, the cannula alone feeding the fluid from the connection sleeve to the dispenser orifice. To this end, the dispenser orifice may be formed by the cannula, or, in a variant, the casing may form the dispenser orifice.

In an advantageous embodiment, the casing is made out of metal, e.g. zamak or steel, so as to impart a cold sensation on contact with the skin. This design is particularly novel, given that the user thinks that the fluid is fed through the metal dispenser head, whereas, in reality, the fluid is fed through the plastics-material cannula of the core. In this way, it is possible to avoid any risk of the fluid oxidizing or deteriorating by coming into contact with the metal. It is even possible to use materials or treatments that are incompatible with the fluid to be dispensed.

In a practical embodiment, the cannula includes a first section that is substantially rectilinear and that extends transversely relative to the axis X, a second section that is bent, and a third section that is inserted into the dispenser endpiece. Advantageously, the endpiece may extend parallel to the axis X along an axis Y, the deformable cannula extends substantially from the axis X to the axis Y, the third section is substantially rectilinear and extends along the axis Y.

In another aspect of the invention, the substantially-rectilinear first section may slope relative to the axis X. Thus, the first section serves to offset the cannula from the axis X, the second section serves to make the cannula parallel with the axis X, and the third section merely extends parallel to the axis X along the axis Y. The cannula is deformed in consequential manner only in its second section.

In an advantageous embodiment, the casing may define a bearing surface that extends downstream from the connection sleeve, intersecting the axis X. This characteristic is also found in the above-mentioned prior art document.

Advantageously, the core forms a collar that is received in stationary manner in a skirt of the casing.

The invention also defines a method of manufacturing a fluid dispenser head for mounting on an axial actuator rod of a dispenser member, such as a pump, the head comprising an inner core and an outer casing, the core forming a connection sleeve of axis X for mounting on the axial actuator rod, the casing forming a dispenser endpiece that is elongate and that is offset relative to the axis X, the method being characterized in that provision is made to make the core with a deformable, rectilinear, sloping cannula, to engage the cannula in the endpiece, to bend the cannula, and to insert the core fully into the casing. The assembly operation is not more complicated than the assembly operation of the dispenser head of document FR 2 860 768, the only difference being that the cannula is deformed during assembly. However, this does not generate an additional operation or manipulation.

The spirit of the invention resides in the core alone forming the fluid feed passage connecting the connection sleeve to the dispenser orifice. The casing serves only as a cover and does not come into contact with the fluid, except possibly at the dispenser orifice. Without complicating either molding or assembly, a dispenser head is obtained that overcomes any risk of internal leakage.

BRIEF DESCRIPTION OF THE DRAWINGS

The invention is described more fully below with reference to the accompanying drawing, which shows an embodiment of the invention by way of non-limiting example.

In the figures:

FIG. 1 is a vertical section view through a dispenser head of the invention in its assembled state;

FIG. 2 is an exploded section view showing the dispenser head during assembly; and FIG. 3 is a view of the dispenser head in FIGS. 1 and 2, associated with a dispenser member.

DETAILED DESCRIPTION OF CERTAIN NON-LIMITING EMBODIMENTS

Reference is made to all of FIGS. 1 to 3 in order to describe the structure and the assembly of a dispenser head made in accordance with a non-limiting embodiment of the invention. The dispenser head comprises two essential component elements, namely an inner core 1 and an outer casing 2, the core 1 being engaged and received in stationary and permanent manner inside the outer casing 2, as can be seen in FIG. 1. Once the dispenser head is mounted on a dispenser member, as shown in FIG. 3, only the outer casing 2 can be seen by the user, the inner core 1 being completely masked.

The inner core 1 is a part, preferably made as a single piece, that may be made by injection-molding an appropriate plastics material. In a variant, it could also be made by assembling together a plurality of separate parts. It is also possible to envisage making the core with various plastics materials by using an over-molding, co-molding, or dual-injection technique. The inner core 1 includes a connection sleeve 11 that extends along an axis X. The connection sleeve 11 is for mounting on an actuator rod 31 of a dispenser member 3, such as a pump or a valve. In general, the connection sleeve 11 is merely force-fitted on the free end of the actuator rod 31. The actuator rod 31 is hollow and serves as a fluid outlet duct for the dispenser member 3. The connection duct 11 is naturally hollow and, at its top end, forms a connection chamber 13 that is also situated on the axis X. The inner core 1 also includes a peripheral collar 12 that extends coaxially around the connection sleeve 11. The collar 12 joins the sleeve 11 at the top end of the sleeve 11, around the connection chamber 13. The chamber 13 communicates directly with a deformable feed cannula 14 that is initially rectilinear, as can be seen in FIG. 2, and that ends up being bent, as can be seen in FIGS. 1 and 3. The cannula 14 has thus been deformed from its initial rectilinear state into its final bent state while assembling the core 1 in the casing 2. It should also be observed that the initial orientation of the cannula 14, as can be seen in FIG. 2, slopes relative to the axis X. The cannula 14 extends from the connection chamber 13 that is on the axis X, and then it extends upwardly and transversely away from the axis X. In FIG. 2, the cannula is rectilinear, such that its free end is at a maximum distance from the axis X, whereas, in FIG. 1, the cannula 14 has been deformed, such that its free end has been moved closer to the axis X, without however returning to the axis X. The cannula may thus be defined as having three different sections, namely: a first section 14a that is connected directly to the connection sleeve 11 and to the transition chamber 13; a second section 14b that is connected to the first section 14a and that is subjected to deformation; and finally a third section 14c having an orientation that has been modified but that remains rectilinear. Thus, the cannula includes two rectilinear sections that remain undeformed, namely the first and third sections 14a and 14c, and an intermediate section 14b that is subjected to deformation so as to enable the change in orientation of the third rectilinear section 14c. By comparing the core 1 in FIGS. 2 and 1, it can clearly be observed that the first section 14a has not been subjected to any deformation, that the section 14b has been bent, and that the third section 14c has not been deformed, but its orientation has been changed. Finally, as shown in FIG. 1, the third section 14c extends parallel to the axis X, along an axis Y that is offset relative to the axis X.

The deformation of the cannula 14 of the inner core 1 is imparted and imposed by the outer casing 2. The casing 2 includes a skirt 22 that is substantially cylindrical and that defines an inner housing 20 for housing the core 1. At its top end, the cylindrical skirt 22 is connected to a bearing surface 21 that intersects the axis X. The user presses, by means of one or more fingers, on the bearing surface 21 so as to move the dispenser head axially along the axis X, so as to actuate the dispenser member 3. The skirt 22 and the bearing surface 21 are connected to an elongate dispenser endpiece 23 that extends along the axis Y, that is parallel to the axis X, but that is offset therefrom. By way of example, the dispenser endpiece 23 may extend along one side of the skirt 22. It can be said that the dispenser endpiece 23 is off-center or offset relative to the axis of symmetry constituted by the axis X. At its top end, the dispenser endpiece 23 defines a dispenser orifice 24 that is situated on the axis Y in this embodiment. It is also possible to envisage making the dispenser orifice 24 a side orifice in a vertical part of the dispenser endpiece 23, in the proximity of its free top end. The outer casing 2 may be made out of any material. But preferably, the outer casing is made out of metal, e.g. zamak or steel, so as to impart a cold sensation on contact with the user's skin. This may be particularly advantageous when the dispensed fluid is for having a soothing effect on the user's skin. In this configuration, the cold sensation provided by the casing further improves the soothing effect. Furthermore, given that the fluid does not (or practically does not) come into contact with the casing, it is even possible to use materials (metal or others) or treatments (e.g. galvanization) that are incompatible with the fluid to be dispensed.

The inner core 1 is inserted into the outer casing 2, as shown in FIG. 2. The still-rectilinear cannula 14 is engaged inside the skirt 22 of the casing. By continuing to insert the core 1 into the casing 2, the free end of the cannula 14 is engaged inside the dispenser endpiece 23. The cannula 14 thus begins to be deformed. By continuing to insert the core 1 into the casing 2, the collar 12 of the core is engaged inside the skirt 22 of the casing. The cannula 14 is then already well deformed. Finally, the core 1 is fully received inside the casing 2, as shown in FIG. 1. The collar 12 is preferably snap-fastened inside the skirt 22. The bearing surface 21 extends just downstream from the connection sleeve 11, intersecting the axis X. The cannula 14 has been deformed in such a manner that its free end comes into intimate contact with the dispenser orifice 24 of the casing 2. The first section 14a has not been subjected to deformation, nor has the third section 14c, with only its orientation being modified. In contrast, the intermediate second section 14b has been bent so as to match the inside shape of the casing 2. It can be said that the second section 14b performs a function of deformable flexible junction between the two sections 14a and 14c that remain undeformed.

By means of the deformable cannula 14, the fluid can be delivered from the connection sleeve 11 to the dispenser orifice 24 without ever coming into contact with the outer casing 2. Any risk of leakage along this path is avoided, and any risk of deterioration of the fluid in contact with the outer casing 2 is also avoided. In the embodiment shown in the drawing, the dispenser orifice 24 is formed by the casing 2, but it is also possible to imagine that the cannula extends to the surface of the casing 2 in such a manner as to form the dispenser orifice.

With reference to FIG. 3, it can be seen that the dispenser head of the invention is entirely suitable for being incorporated with a conventional dispenser member 3 that may be a pump or a valve. The connection sleeve 11 is engaged on the actuator rod 31 that is axially movable down and up along the axis X. The dispenser member is provided with a fastener ring 4 for mounting in stationary and leaktight manner on a reservoir neck (not shown). It should be observed that the bottom end of the skirt 22 of the casing 2 is inserted into an annular groove 42 that is formed by the fastener ring 4. Thus, the inner core 1 is completely masked, only the outer casing 22 can be seen by the user. The user has the impression that the dispenser head is formed only by the outer casing 2: this is reinforced further by the fact that the free end of the cannula 14 does not form the dispenser orifice 24. When the outer casing 2 is made out of metal, the user may think that the fluid is delivered directly in contact with the metal. Optionally, the dispenser head may be covered by a protective cap 5 that is mounted on the fastener ring 4.

In the embodiment used to illustrate the present invention, the cannula 14 remains undeformed at its third section 14c. However, in the context of the present invention, it is possible to envisage that the third section 14c is also deformed while being inserted into the outer casing 2. It is also possible to imagine that the dispenser endpiece 23 does not extend parallel to the axis X: it may be sloping, or even bent.

The invention thus provides a novel dispenser head having a dispenser endpiece that is elongate and offset, and in which head, fluid feed takes place only via the inner core 1.

The invention claimed is:

1. A fluid dispenser head for mounting on an axial actuator rod (31) of a dispenser member (3), the head comprising an inner core (1) and an outer casing (2), the core (1) forming a connection sleeve (11) of axis (X) for mounting on the axial actuator rod (31), the casing (2) forming a dispenser endpiece (23) that is elongate and that is offset relative to the axis (X), the core (1) forms a deformable cannula (14) that is connected to the connection sleeve (11) and that extends in the endpiece (23) of the casing (2), the cannula being deformable so as to bend from an initial state of being rectilinear over an entire length of the cannula and sloping relative to the axis (X), to a bent state in which the cannula is deformed while inserted into the endpiece (23) so as to fit in the endpiece.

2. A dispenser head according to claim 1, wherein the cannula (14) presents a wall thickness that is less than the wall thickness of the connection sleeve (11) so as to impart flexibility thereto.

3. A dispenser head according to claim 1, wherein the cannula (14) extends over substantially the entire length of the endpiece (23).

4. A dispenser head according to claim 1, wherein the casing (2) forms a dispenser orifice (24).

5. A dispenser head according to claim 1, wherein the casing (2) is made out of metal so as to impart a cold sensation on contact with the skin.

6. The dispenser head according to claim 5, wherein the metal is an alloy comprising zinc, aluminium, magnesium, and copper or is a steel.

7. A dispenser head according to claim 1, wherein the cannula (14) includes a first section (14a) that is substantially rectilinear and that extends transversely relative to the axis X, a second section (14b) that is bent, and a third section (14c) that is inserted into the dispenser endpiece (23).

8. A dispenser head according to claim 7, wherein the endpiece extends parallel to the axis X along an axis Y, the deformable cannula extends substantially from the axis X to the axis Y, the third section (14c) is substantially rectilinear and extends along the axis Y.

9. A dispenser head according to claim 7, wherein the substantially-rectilinear first section (14a) slopes relative to the axis X.

10. A dispenser head according to claim 1, wherein the casing (2) defines a bearing surface (21) that extends downstream from the connection sleeve, intersecting the axis X.

11. A dispenser head according to claim 1, wherein the core (1) forms a collar (12) that is received in stationary manner in a skirt (22) of the casing (2).

12. A method of manufacturing a fluid dispenser head for mounting on an axial actuator rod (31) of a dispenser member (3), comprising:
providing an outer casing (2), the casing (2) forming a dispenser endpiece (23) that is elongate and that is offset relative to the a first axis (X);
providing a core (1) forming a connection sleeve (11) along the central axis (X) for mounting on the axial actuator rod (31), the core, prior to assembly with the outer casing, is a deformable, rectilinear, sloping cannula (14) extending at an angle relative to the first axis; and
engaging the cannula (14) in the endpiece (23), by bending and fully inserting the cannula (14) into the casing (2).

13. The dispenser head according to claim 1, wherein the dispenser member is a pump.

14. A fluid dispenser head for mounting on an axial actuator rod of a dispenser member, the head comprising:
an inner core; and
an outer casing;
the core comprising a connection sleeve extending along a first axis for mounting on the axial actuator rod;
the casing comprising a dispenser endpiece that is elongate and that is offset relative to the first axis;

the core comprising a deformable cannula that is in fluid communication with the connection sleeve and that extends inside the endpiece of the casing;

the cannula is deformable over an entire length of the cannula so as to bend from an initial state, prior to assembly with the endpiece, that is rectilinear and that extends at an angle relative to the first axis to an assembled state in which the cannula, after being deformed while fully inserted into the endpiece, is bent along the endpiece.

* * * * *